(12) United States Patent
Gao et al.

(10) Patent No.: US 12,109,313 B2
(45) Date of Patent: *Oct. 8, 2024

(54) SOLUBLE FIBER LOZENGE

(71) Applicant: Altria Client Services LLC, Richmond, VA (US)

(72) Inventors: Feng Gao, Midlothian, VA (US); Diane L. Gee, Chesterfield, VA (US); Shuzhong Zhuang, Glen Allen, VA (US); Phillip M. Hulan, Midlothian, VA (US); William J. Burke, Nashville, TN (US); Gerd Kobal, Sandy Hook, VA (US)

(73) Assignee: Altria Client Services LLC, Richmond, VA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/066,730

(22) Filed: Dec. 15, 2022

(65) Prior Publication Data

US 2023/0121049 A1   Apr. 20, 2023

Related U.S. Application Data

(63) Continuation of application No. 16/132,728, filed on Sep. 17, 2018, now Pat. No. 11,554,099, which is a continuation of application No. 14/505,988, filed on Oct. 3, 2014, now Pat. No. 10,105,320.

(60) Provisional application No. 61/886,373, filed on Oct. 3, 2013.

(51) Int. Cl.
| | | |
|---|---|---|
| *A61K 9/20* | (2006.01) | |
| *A23G 3/34* | (2006.01) | |
| *A23G 3/38* | (2006.01) | |
| *A23G 3/42* | (2006.01) | |
| *A61K 8/73* | (2006.01) | |
| *A61K 9/00* | (2006.01) | |
| *A61Q 11/00* | (2006.01) | |

(52) U.S. Cl.
CPC .......... *A61K 9/2059* (2013.01); *A23G 3/0021* (2013.01); *A23G 3/38* (2013.01); *A23G 3/42* (2013.01); *A61K 8/732* (2013.01); *A61Q 11/00* (2013.01); *A23V 2002/00* (2013.01); *A61K 9/0056* (2013.01)

(58) Field of Classification Search
CPC .. C08B 1/00; A61K 9/50; A61K 31/71; A61K 9/20; A61K 8/0216; A61K 2800/92; A23G 3/00
USPC ........................................ 426/660, 548, 658
See application file for complete search history.

(56) References Cited

U.S. PATENT DOCUMENTS

| | | |
|---|---|---|
| 444,828 A | 1/1891 | Groshon |
| 2,162,738 A | 6/1939 | McCoy |
| 2,791,509 A | 5/1957 | Cosler |
| 3,139,436 A | 6/1964 | Bicking |
| 3,271,256 A | 9/1966 | Frey |
| 3,396,735 A | 8/1968 | Von Bethmann et al. |
| 4,153,063 A | 5/1979 | Roselius et al. |
| 4,259,314 A | 3/1981 | Lowey |
| 4,448,208 A | 5/1984 | Friedrich et al. |
| 4,516,590 A | 5/1985 | Teng |
| 4,528,993 A | 7/1985 | Sensabaugh, Jr. et al. |
| 4,647,459 A | 3/1987 | Peters et al. |
| 4,660,577 A | 4/1987 | Sensabaugh et al. |
| 4,848,373 A | 7/1989 | Lenkey |
| 4,987,907 A | 1/1991 | Townend |
| 5,167,964 A * | 12/1992 | Muhammad ......... A61K 9/5078 424/440 |
| 5,236,719 A | 8/1993 | Meyers et al. |
| 5,284,163 A | 2/1994 | Knudsen et al. |
| 5,372,149 A | 12/1994 | Roth et al. |
| 5,380,717 A | 1/1995 | Ohkuma et al. |
| 5,410,035 A | 4/1995 | Wakabayashi et al. |
| 5,487,792 A | 1/1996 | King et al. |
| 5,525,351 A | 6/1996 | Dam |
| 5,549,906 A | 8/1996 | Santus |

(Continued)

FOREIGN PATENT DOCUMENTS

| | | |
|---|---|---|
| DE | 19811167 A1 | 9/1999 |
| EP | 1086691 A1 | 3/2001 |

(Continued)

OTHER PUBLICATIONS

European Office Action for EP Application 20209413.2 dated Mar. 3, 2023 (5 pages).
"Particle Size Conversion Table," SIGMA-ALDRICH, 2003-2004, [online], retreived from the Internet Mar. 29, 2017, <URL: http://www.sigmaaldrich.com/chemistry/stockroom-reagents,learning-center/technical-library/particle-sizze-conversion.html>.
Avaltroni et al., "Maltodextrin molecular weight distribution influence on the glass transition temperature and viscosity in aqueous solutions," Carbohyd Polymers 58:323-334, 2004.

(Continued)

*Primary Examiner* — Walter E Webb
(74) *Attorney, Agent, or Firm* — Harness, Dickey & Pierce, P.L.C.

(57) ABSTRACT

A soluble fiber lozenge in includes a body that is partially or wholly receivable in an oral cavity. The body includes a soluble-fiber matrix and one or more additives in the soluble-fiber matrix. A soluble fiber lozenge provided herein includes at least 40 weight percent of soluble fiber. Soluble fiber in soluble fiber lozenge can include maltodextrin. The soluble fiber lozenge is adapted to release one or more additives from the body when the body is received within the oral cavity of a consumer and exposed to saliva. A method of making soluble fiber lozenges includes forming a molten mixture of at least 40 weight percent soluble fiber, one or more additives, and less than 15 weight percent water while maintaining a mixture temperature of less than 200° C. and portioning the molten mixture into a plurality of soluble fiber lozenges.

19 Claims, 5 Drawing Sheets

(56) References Cited

U.S. PATENT DOCUMENTS

| | | | |
|---|---|---|---|
| 5,629,042 A * | 5/1997 | Serpelloni | A23G 3/42 426/660 |
| 6,203,842 B1 | 3/2001 | Reddy | |
| 7,798,151 B2 | 9/2010 | Krukonis et al. | |
| 9,351,936 B2 | 5/2016 | Gao et al. | |
| 9,943,511 B2 | 4/2018 | Gao et al. | |
| 9,946,511 B2 | 4/2018 | Gelfenbeyn et al. | |
| 9,999,243 B2 | 6/2018 | Gao et al. | |
| 10,105,320 B2 | 10/2018 | Gao et al. | |
| 10,244,786 B2 | 4/2019 | Gao et al. | |
| 10,702,516 B2 | 7/2020 | Gao et al. | |
| 2002/0076433 A1 | 6/2002 | D'Amelia et al. | |
| 2004/0118422 A1 | 6/2004 | Lundin et al. | |
| 2004/0253307 A1 | 12/2004 | Hague et al. | |
| 2005/0053665 A1 | 3/2005 | Ek et al. | |
| 2005/0123502 A1 | 6/2005 | Chan et al. | |
| 2005/0152932 A1 | 7/2005 | Normand et al. | |
| 2005/0178398 A1 | 8/2005 | Breslin et al. | |
| 2005/0226925 A1 | 10/2005 | Singh | |
| 2005/0244521 A1 | 11/2005 | Strickland | |
| 2006/0171994 A1 | 8/2006 | Dupinay et al. | |
| 2007/0144544 A1 | 6/2007 | Cai et al. | |
| 2007/0172511 A1 | 7/2007 | Harrison et al. | |
| 2008/0209586 A1 | 8/2008 | Nielsen et al. | |
| 2009/0293889 A1 | 12/2009 | Kumar et al. | |
| 2010/0010101 A1 | 1/2010 | Cherukuri | |
| 2011/0110880 A1 | 5/2011 | Chen | |
| 2011/0139164 A1 | 6/2011 | Mua et al. | |
| 2011/0165253 A1 | 7/2011 | Roehrich | |
| 2011/0200670 A1 | 8/2011 | Thakkar | |
| 2012/0031414 A1 | 2/2012 | Atchley et al. | |
| 2012/0053108 A1 | 3/2012 | Glenn, Jr. et al. | |
| 2012/0060854 A1 | 3/2012 | Chen et al. | |
| 2013/0071476 A1 | 3/2013 | Cherukuri | |
| 2013/0186417 A1 | 7/2013 | Gao et al. | |
| 2013/0186418 A1 | 7/2013 | Gao et al. | |
| 2013/0206150 A1 | 8/2013 | Duggins et al. | |
| 2013/0260150 A1 | 10/2013 | Grivei et al. | |
| 2013/0284193 A1 | 10/2013 | Matsumoto et al. | |
| 2015/0020818 A1 | 1/2015 | Gao et al. | |
| 2015/0096576 A1 | 4/2015 | Gao et al. | |
| 2021/0169127 A1 | 6/2021 | Gao et al. | |

FOREIGN PATENT DOCUMENTS

| | | | | |
|---|---|---|---|---|
| EP | 2177213 A1 | 4/2010 | | |
| WO | WO-9723201 A1 | 7/1997 | | |
| WO | WO-200176383 A1 | 10/2001 | | |
| WO | WO2003/020736 | * | 3/2003 | C07H 15/00 |
| WO | 2007100721 A2 | 9/2007 | | |
| WO | WO-2009/134947 A1 | 11/2009 | | |
| WO | WO-2010-044736 A1 | 4/2010 | | |
| WO | WO-2011064797 A2 | 6/2011 | | |

OTHER PUBLICATIONS

Fitzpatrick et al., "Comparing the caking behaviours of skim milk powder, amorphous maltodextrin, and crystalline common salt," Powder Technology 204(1):131-137, 2010.

Gonnissen et al., "Develpoement of directly compressible Powders via Co-Spraying," Eur J Pharma Biopharma 67:220, 2007.

International Preliminary Report on Patentability in International Application No. PCT/US2014/059148, mailed Apr. 14, 2016, 6 pages.

Patel et al., "Advanes is oral transmucosal drug delivery." J Control Release Jul. 30, 2011; 153(2): 106-16.

International Search Report and Written Opinion in International Appication No. PCT/US2014/059148, mailed Dec. 12, 2014, 9 pages.

Tso (1999, Chapter 1 in Tobacco, Production, Chemistry and Technology, Davis & Nielsen, eds., Blackwell Publishing, Oxford).

Patel et al., "Advances in oral transmucosal drug delivery." J Control Release Jul. 30, 2011; 153(2): 106-16.

European Search Report for corresponding Application No. 14790894. 1-1114, dated Jun. 11, 2019.

Extended European Search Report dated Aug. 25, 2021 for EP Application No. 20209413.2.

Notice of Allowance for U.S. Appl. No. 14/506,003 dated Nov. 21, 2018.

Non-Final Office Action for U.S. Appl. No. 14/506,003 dated Apr. 5, 2017.

Final Office Action for U.S. Appl. No. 14/506,003 dated Nov. 24, 2017.

Non-Final Office Action for U.S. Appl. No. 14/506,003 dated Jun. 20, 2018.

Notice of Allowance for U.S. Appl. No. 16/370,020 dated Oct. 26, 2020.

Non-Final Office Action for U.S. Appl. No. 16/370,020, dated Jul. 15, 2020.

Non-Final Office Action for U.S. Appl. No. 14/506,002 dated Mar. 31, 2017.

Notice of Allowance for U.S. Appl. No. 14/506,002 dated Oct. 17, 2017.

Non-Final Office Action for U.S. Appl. No. 14/506,093 dated Sep. 4, 2015.

Notice of Allowance for U.S. Appl. No. 14/506,093 dated Jan. 29, 2016.

Non-Final Office Action for U.S. Appl. No. 15/142,048 dated Mar. 14, 2017.

Notice of Allowance for U.S. Appl. No. 15/142,048 dated Aug. 28, 2017.

Notice of Allowance for U.S. Appl. No. 15/142,048 dated Dec. 15, 2017.

Non-Final Office Action for U.S. Appl. No. 15/954,150 dated Mar. 5, 2019.

Final Office Action for U.S. Appl. No. 15/954,150 dated Sep. 9, 2019.

Notice of Allowance for U.S. Appl. No. 15/954,150 dated Mar. 11, 2020.

Notice of Allowance for U.S. Appl. No. 16/897,966, dated May 26, 2021.

Definition of matrix, The Free Dictionary, 5 pages, 1991 to 2016, [online], retrieved from the internet, [retrieved Oct. 11, 2017], <URL: http://www.thefreedictionary.com/matrix>.

Fitzpatrick, et al. "Comparing the caking behaviours of skim milk, powder, amorphous maltodextrin and crystalline common salt," Powder Technology, V. 204, No. 1, 2010, pp. 131-137. [online], retrieved from the internet, [retrieved Mar. 26, 2017], <URL: http://www.sciencedirect.com/science/article/pii/ S0032591010003761>.

"Particle Size Conversation Table," SIGMA-ALDRICH, 2003-2004, [online], retreieved from the internet, [retreieved Mar. 29, 2017], <URL: http://sigmaaldrich.com/chemistry/stockroom-reagents/ learning-ceneter/technical-library/particle-size-conversation.html>.

Avaltroni et al. "Maltodextrin molecular weight distribution influence on the glass transition temperature and viscosity in aqueous solutions" Carbohyd Polymers 58 (2004), 323-334, {online], retrieved fromthe internet, [retrieved Mar. 27, 2017], <URL: https://www. researchgate.net/publication/223748654_Maltodextrin_molecular_ weight_distribution_in.

Definition of lozenge, The Free Dictionary, 3 pages, 2002, online, retrieved from the Internet [retrieved Mar. 30, 2017], <URL: http://www.thefreedictionary.com/lozenge>.

Notice of Allowance for U.S. Appl. No. 14/506,002 dated Feb. 20, 2018.

Y. Gonnissen, et al, Development of Directly Compressible Powders via Co- Spraying, 67 Eur. J Pharma. Biopharma. 220 (Year:2007).

Patel et al., "Advances in oral transmucosal drug delivery," J. Control Release, Jul. 30, 2011, vol. 153, No. 2, pp. 106-116.

* cited by examiner

SOLUBLE FIBER LOZENGE

CROSS REFERENCE TO RELATED APPLICATIONS

This application is a continuation of U.S. application Ser. No. 16/132,728, filed Sep. 17, 2018, which is a continuation of U.S. application Ser. No. 14/505,988, filed Oct. 3, 2014, which claims the benefit of priority under 35 U.S.C. § 119(e) to U.S. Application No. 61/886,373 filed Oct. 3, 2013. The entire contents of each of which are incorporated herein by reference.

TECHNICAL FIELD

This document relates to soluble fiber lozenges and methods for making soluble fiber lozenges. For example, a soluble fiber lozenge can include one or more additives within a soluble-fiber matrix (e.g., maltodextrin).

BACKGROUND

Oral products providing flavor and/or one or more active ingredients are well known. One such oral product is chewing gum. Other oral products include hard pieces (e.g., mints). Softer gelatin-based oral products are also known. Pharmaceutical and therapeutic products (e.g., cough-suppressant lozenges) can also be provided in a solid form for oral consumption. The flavor release and/or active agent release characteristics for an oral product are important for providing an improved consumer product.

SUMMARY

A soluble fiber lozenge provided herein provides a satisfying tactile and/or flavor experience. A soluble fiber lozenge provided herein includes a body that is at least partially receivable in an oral cavity of a consumer. In some cases, a soluble fiber lozenge provided herein includes a body that is wholly receivable in an oral cavity. The body can include a soluble-fiber matrix and one or more additives dispersed in the soluble-fiber matrix. In some cases, a soluble fiber lozenge provided herein includes at least 40 weight percent of soluble fiber. In some cases, soluble fiber in a soluble fiber lozenge provided herein can include maltodextrin. A soluble fiber lozenge provided herein can be adapted to release one or more additives from the body when the body is received within the oral cavity of a consumer and exposed to saliva. A body of a soluble fiber lozenge provided herein can be a single phase structure. In some cases, the body of a soluble fiber lozenge provided herein can be amorphous.

Soluble fiber lozenges provided herein, in some cases, include one or more additives selected from the categories of flavorants, sweeteners, vitamins, minerals, therapeutic agents, nutraceuticals, energizing agents, soothing agents, coloring agents, amino acids, chemesthic agents, antioxidants, food grade emulsifiers, pH modifiers, botanicals, teeth whitening agents, and/or alkaloids (e.g., caffeine). Combinations of additives (e.g., sweeteners, flavorants, and caffeine) can be combined to provide a favorable tactile and flavor experience.

A method of making soluble fiber lozenges provided herein includes forming a molten mixture of at least 40 weight percent soluble fiber, one or more additives, and less than 15 weight percent water while maintaining a mixture temperature of less than 180° C. and portioning the molten mixture into a plurality of soluble fiber lozenges. In some cases, the ingredients can be mixed to form the molten mixture in an extruder, flattened into a sheet of a predetermined thickness as it leaves the extruder, and individual soluble fiber lozenges cut from the sheet before the sheet cools below the glass transition temperature range of the molten mixture. Unlike a traditional lozenge, which incorporates sugars or sugar alcohols that are heated to a temperature such that caramelization occurs, methods provided herein include heating the molten mixture to form a solution of or dispersion of one or more additives in the soluble fiber without significant crosslinking. Because certain additives (e.g., therapeutic agents) degradation can be accelerated when exposed to elevated temperatures over extended periods of time, the temperature of a molten mixture provided herein can be maintained at a temperature of 200° C. or below over a residence time of five to ten minutes or less (for example if an extrusion process is utilized). In some cases, a molten mixture provided herein is heated to a temperature of between 80° C. and 200° C. In some cases, a molten mixture provided herein is heated to a temperature of between 100° C. and 110° C. When cooled below its glass transition temperature, a molten mixture provided herein solidifies into an amorphous, non-porous soluble fiber matrix containing one or more additives. Because the soluble fibers do not become crosslinked, the soluble fibers remain soluble and thus dissolve when placed in consumer consumer's mouth.

A soluble fiber lozenge body can be rigid and brittle. In some cases, a body provided herein can have a glass transition temperature greater than 37° C. In some cases, a body provided herein can have a glass transition temperature of between 50° C. and 120° C. In some cases, a body provided herein can have a glass transition temperature of between 80° C. and 100° C. In some cases, a body provided herein having 90 weight percent maltodextrin can have a glass transition temperature of approximately 98° C. A soluble fiber lozenge provided herein can have a coating over the body. In some cases, the body of a soluble fiber lozenge provided herein can be non-porous.

A soluble fiber lozenge body can include at least 40 weight percent of soluble fiber. In some cases, the soluble fiber lozenge body includes at least 50 weight percent of soluble fiber. In some cases, the soluble fiber lozenge body includes at least 60 weight percent of soluble fiber. In some cases, the soluble fiber lozenge body includes at least 70 weight percent of soluble fiber. In some cases, the soluble fiber lozenge body includes at least 75 weight percent of soluble fiber. In some cases, the soluble fiber lozenge body includes at least 80 weight percent of soluble fiber. In some cases, the soluble fiber lozenge body includes at least 85 weight percent of soluble fiber. In some cases, the soluble fiber lozenge body includes at least 90 weight percent of soluble fiber. In some cases, the soluble fiber lozenge body includes at least 95 weight percent soluble fiber. In some cases, the soluble fiber can include maltodextrin, psyllium, inulin, arabinoxylans, cellulose, resistant starch, resistant dextrins, lignin, pectins, beta-glucans, and oligosaccharides or a combination thereof. In some cases, a soluble fiber lozenge body can include at least 40 weight percent maltodextrin. In some cases, the soluble fiber lozenge body includes at least 50 weight percent maltodextrin. In some cases, the soluble fiber lozenge body includes at least 60 weight percent maltodextrin. In some cases, the soluble fiber lozenge body includes at least 70 weight percent maltodextrin. In some cases, the soluble fiber lozenge body includes at least 75 weight percent maltodextrin. In some cases, the soluble fiber lozenge body includes at least 80 weight percent maltodextrin. In some cases, the soluble fiber lozenge body includes at least 85 weight percent maltodextrin. In some cases, the soluble fiber lozenge body includes at least 90 weight percent maltodextrin. In some cases, the soluble fiber lozenge body includes at least 95 weight percent maltodextrin.

In some cases, a soluble fiber lozenge provided herein can include a digestion-resistant soluble fiber (e.g., maltodextrins.) Suitable maltodextrins include those that are soluble in water up to 70% at 20° C., have a viscosity of about 15 cps for a 30% solution at 30° C., a DE in the range of about 6-16, and contain random $\alpha$-1,2, $\alpha$-1,3, $\alpha$-1,4, $\beta$-1,2, $\beta$-1,3 and $\beta$-1,4 glucose linkages in addition to the normal $\alpha$-1,4 glucose linkages found in partially hydrolyzed starch. See, e.g., U.S. Pat. Nos. 5,410,035; 5,380,717. For example, Fibersol®-2 is a maltodextrin of DE 6-10 processed from corn starch using hydrochloric acid and enzymes, which can be used as the soluble fiber in a soluble fiber lozenge provided herein. Fibersol®-2 is partially indigestible because human digestive enzymes are incapable of digesting $\beta$ 1,2, $\beta$ 1,3 and $\beta$ 1,6 glucose bonds. See, e.g., U.S. Pat. No. 6,203,842. Other starch sources such as potato, rice, wheat, barley, peas, beans, lentils, oats, or tapioca can be processed to form digestion-resistant soluble fiber. A digestion resistant soluble fiber includes starch linkages that cannot be hydrolyzed by enzymes of the human digestive tract. Soluble fiber used in a soluble fiber lozenge provided herein can be a soluble fiber generally recognized as safe ("GRAS") by the Food and Drug Administration or another appropriate private, state, or national regulatory agency.

A soluble fiber lozenge provided herein can, in some cases, include up to 15 weight percent water. In some cases, a soluble fiber lozenge provided herein can include between 2 weight percent and 15 weight percent water. In some cases, a soluble fiber lozenge provided herein can include between 3 weight percent and 10 weight percent water. In some cases, a soluble fiber lozenge provided herein can include between 4 weight percent and 7 weight percent water.

A soluble fiber lozenge provided herein can include a sweetener dispersed therein. Suitable sweeteners include saccharine, sucralose, aspartame, acesulfame potassium, and combinations thereof. In some cases, a soluble fiber lozenge provided herein can be substantially free of sugars and sugar alcohols. For example, a soluble fiber lozenge can be substantially free of sugars and sugar alcohols, but include non-nutritive sweeteners. In some cases, a soluble fiber lozenge provided herein can include non-caramelized sugars and/or sugar alcohols in a percentage of no more than 25 weight percent. For example, mannitol and/or sorbitol can be added to reduce the glass transition temperature of a molten mixture provided herein. When included, sugars and sugar alcohols in a molten mixture form a solution with the soluble fiber. Sugars and sugar alcohols can alter the glass transition temperature of a molten mixture provided herein. When cooled below the glass transition temperature, a solution of soluble fiber and sugar alcohols remains an amorphous, single-phase, non-crosslinked structure.

A soluble fiber lozenge provided herein can include one or more flavorants as an additive. The flavorants can be natural or artificial. Flavorants can be selected from the following: licorice, wintergreen, cherry and berry type flavorants, Drambuie, bourbon, scotch, whiskey, spearmint, peppermint, lavender, cinnamon, cardamon, apium graveolents, clove, cascarilla, nutmeg, sandalwood, bergamot, geranium, honey essence, rose oil, vanilla, lemon oil, orange oil, Japanese mint, cassia, caraway, cognac, jasmin, chamomile, menthol, ylang ylang, sage, fennel, pimenta, ginger, chai, anise, coriander, coffee, mint oils from a species of the genus Mentha, cocoa, and combinations thereof. Synthetic flavorants can also be used. The particular combination of flavorants can be selected from flavorants that are GRAS in a particular country, such as the United States. Flavorants can also be included in the soluble fiber lozenge as encapsulated flavorants.

A soluble fiber lozenge provided herein can include a plasticizer dispersed in the soluble-fiber matrix. For example, the plasticizer can be propylene glycol, triacetin, glycerin, vegetable oil, partially hydrogenated oil, triglycerides, triacetin, or a combination thereof.

A body of a soluble fiber lozenge provided herein can have a variety of different shapes, some of which include disk, heart, rectangle, and square. In some cases, a body of a soluble fiber lozenge provided herein can have rounded corners. In some cases, the body of the soluble fiber lozenge can be spherical. According to certain cases, the body can have a length or width of between 1 mm and 25 mm and a thickness of between 1 mm and 25 mm. In some cases, the body can have a length or width of between 5 mm and 15 mm and a thickness of between 2 mm and 5 mm. In some cases, a soluble fiber lozenge provided herein can include a colorant. For example, a body of a soluble fiber lozenge provided herein can include titanium dioxide, which can provide the body with a white color. In some cases, a coating on the body can include a colorant.

A method of forming soluble fiber lozenges can include forming a molten mixture of at least 40 weight percent soluble fiber, one or more additives, and less than 15 weight percent water, while maintaining a mixture temperature of less than 200° C. In some cases, the molten mixture includes at less than 13 weight percent, less than 10 weight percent, less than 8 weight percent, less than 7 weight percent, less than 6 weight percent, or less than 5 weight percent water. In some cases, the molten mixture includes at least 3 weight percent, at least 4 weight percent, at least 6 weight percent, or at least 7 weight percent water. The one or more additives can include one or more additives selected from colorants, sweeteners, flavorants, plasticizers, antioxidants, and combinations thereof. In some cases, the molten mixture is substantially free of cellulose fiber, and/or sugar alcohols.

In some cases, the molten mixture provided herein is formed in an extruder. The extruder can be a multi-staged extruder having different sections that are heated to different temperatures and/or have different ingredients introduced. In some cases, an extruder provided herein can include multiple stages and can be used in a method provided herein in a process where the maximum temperature in any stage is no more than 200° C. (e.g., no more than 200° C., no more than 150° C., no more than 120° C., no more than 110° C., or no more than 105° C.). In some cases, the molten mixture can be heated to a maximum temperature of greater than the molten mixture's Tg and less than 200° C.

Portioning the molten mixture provided herein can be accomplished using any suitable method. In some cases, the molten mixture can be formed into a sheet of a predetermined thickness as it comes out of the extruder and individual soluble fiber lozenges cut from the sheet with a stamping die. A method provided herein can further include cooling soluble fiber lozenges and packaging soluble fiber lozenges.

The details of one or more embodiments of the subject matter described in this specification are set forth in the accompanying drawings and the description below. Other features, aspects, and advantages of the subject matter will become apparent from the description, the drawings, and the claims.

DETAILED DESCRIPTION

The soluble fiber lozenges described herein include one or more additives in a soluble-fiber matrix. One or more additives can be dispersed in the soluble-fiber matrix such that is the one or more additives are released from the soluble fiber lozenge as it dissolves when the soluble fiber lozenge is received within the oral cavity and exposed to saliva. The soluble fiber lozenges described herein can provide a favorable additive release profile and tactile experience. In some cases, a soluble fiber lozenge provided herein includes one or more additives in solution with soluble fiber of the matrix.

Soluble fiber lozenges provided herein, in some cases, include one or more additives selected from the categories of flavorants, sweeteners, vitamins, minerals, therapeutic agents, nutraceuticals, energizing agents, soothing agents, coloring agents, amino acids, chemesthic agents, antioxidants, food grade emulsifiers, pH modifiers, botanicals, teeth whitening agents, and/or alkaloids (e.g., caffeine). Combinations of additives (e.g., sweeteners, flavorants, and caffeine) can be combined to provide a favorable tactile and flavor experience.

A soluble fiber lozenge provided herein can take up to 1 hour to dissolve when placed in a consumer's mouth. In some cases, a soluble fiber lozenge provided herein can take between 1 minute and 30 minutes to dissolve when placed in a consumer's mouth if the consumer does not masticate the soluble fiber lozenge. In some cases, a soluble fiber lozenge provided herein can take between 2 minutes and 15 minutes to dissolve when placed in a consumer's mouth if the consumer does not masticate the soluble fiber lozenge.

Soluble fiber lozenges provided herein can be substantially free of cellulose fibers. In some cases, a soluble fiber lozenge provided herein includes up to 10 weight percent cellulosic fibers. Cellulosic fibers used in a soluble fiber lozenge provided herein can have an average fiber length of less than 200 micrometers. In particular cases, cellulosic fibers in a soluble fiber lozenge provided herein have sizes between 25 and 125 micrometers.

In addition to additives, sweeteners, and flavorants, the soluble fiber lozenge can also include fillers, plasticizers, antioxidants, and/or processing aids. Fillers can also be included in the soluble-fiber matrix to alter the texture or pliability of the soluble fiber lozenge. The soluble-fiber matrix can also include plasticizers (e.g., propylene glycol), which can increase the softness of a soluble fiber lozenge provided herein. Antioxidants can be used to preserve in the soluble fiber lozenge. Processing aids can also be present in the soluble fiber lozenge and be used to facilitate shaping processes.

Lozenge Shapes and Packaging

Figure 1A:
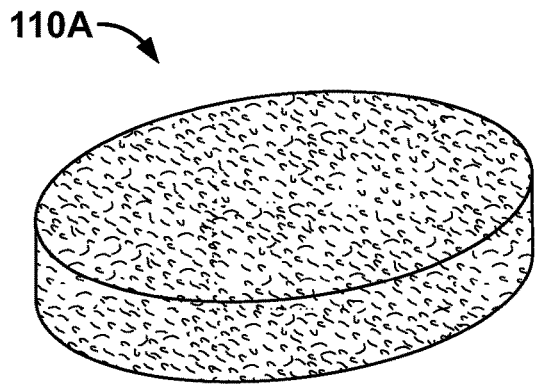
FIGS. 1A-1O illustrates various exemplary shapes of soluble fiber lozenges provided herein.
Figure 1B:
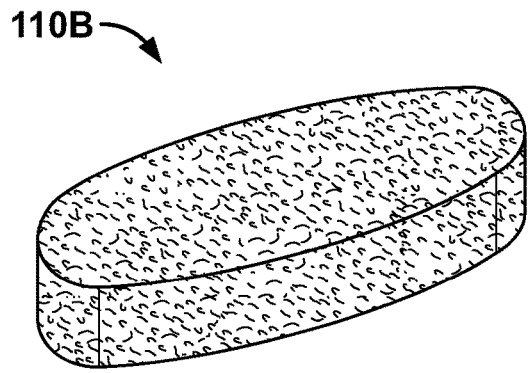
Figure 1C:
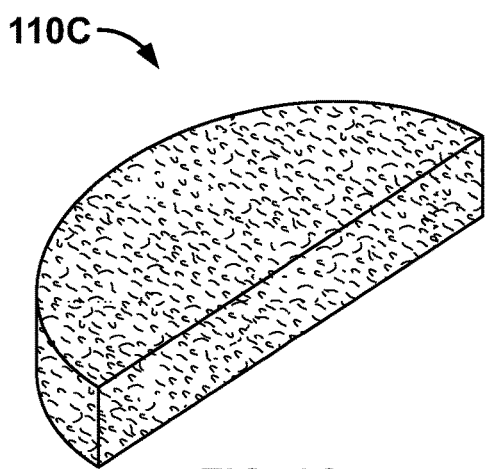
Figure 1D:
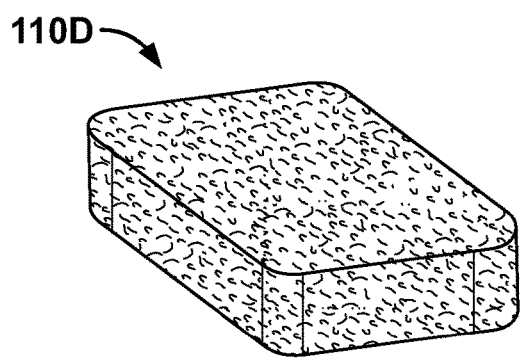
Figure 1E:
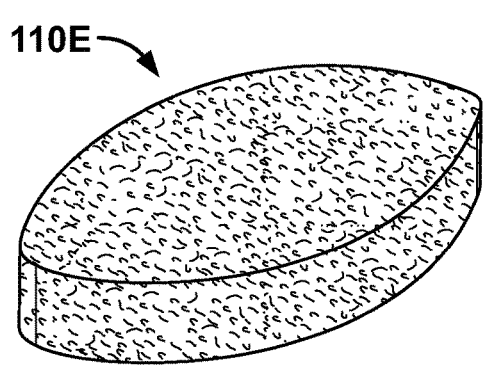
Figure 1F:
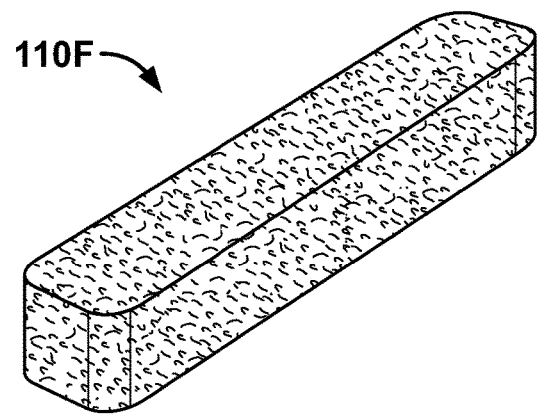
Figure 1G:
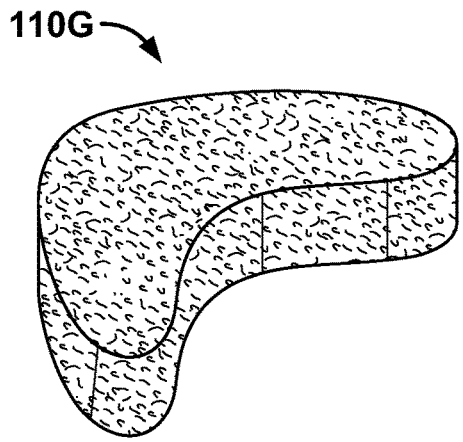
Figure 1H:
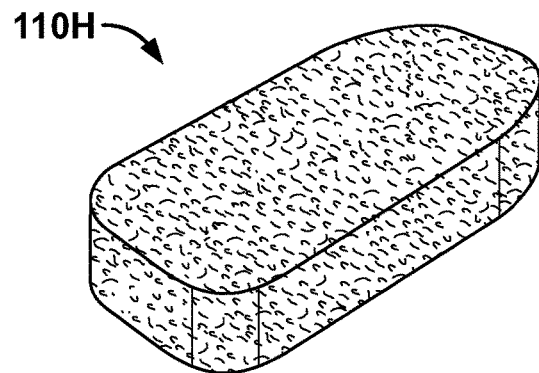
Figure 1I:
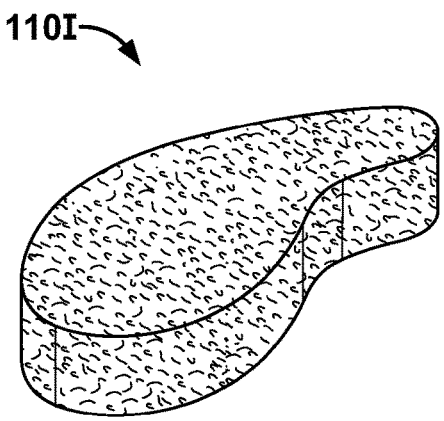
Figure 1J:
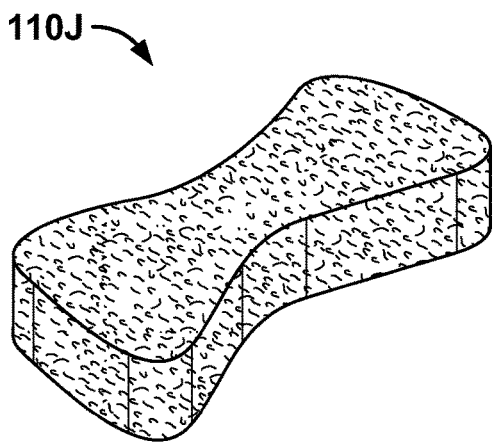
Figure 1K:
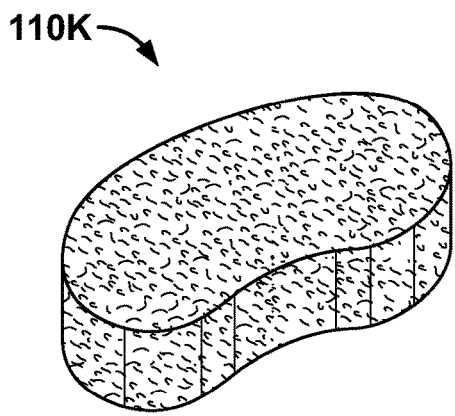
Figure 1L:
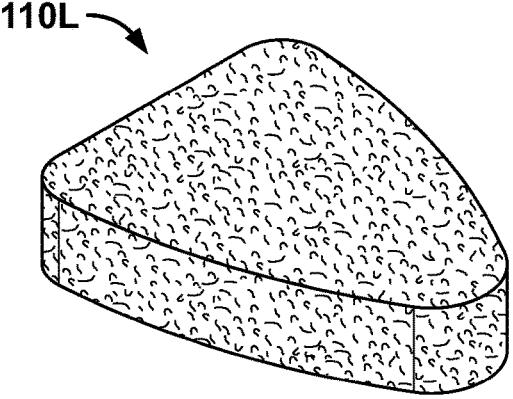
Figure 1M:
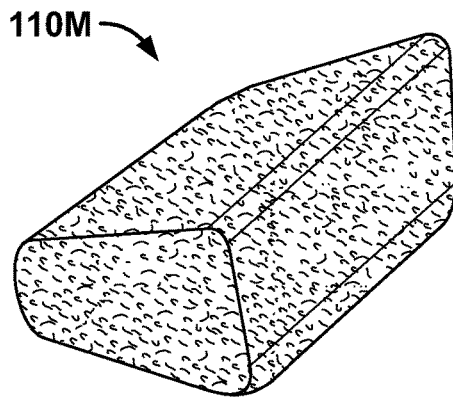
Figure 1N:
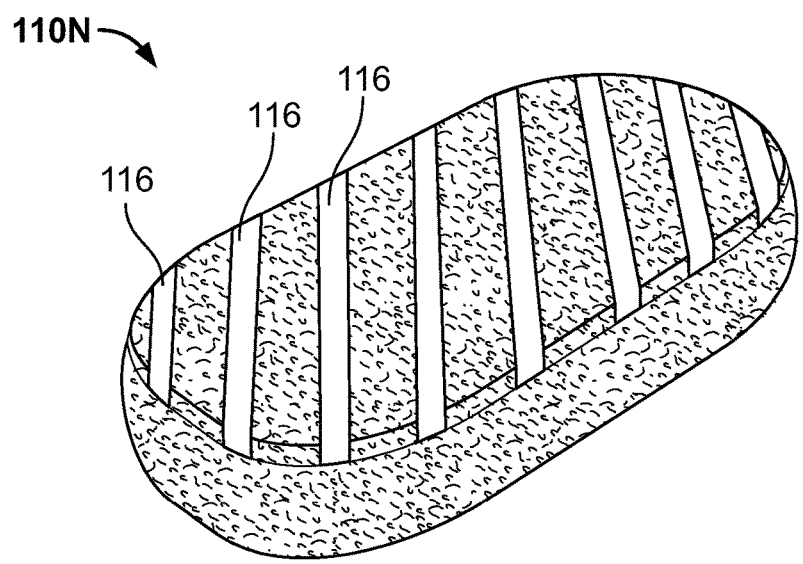

Referring now to FIGS. 1A-1N, a soluble fiber lozenge provided herein can be molded into any desired shape. For example, referring to FIGS. 1A-1L, a soluble fiber lozenge provided can be formed in a shape that promotes improved positioning in the oral cavity, improved packaging characteristics, or both. In some circumstances, a soluble fiber lozenge 110A-L can be configured to be: (A) an elliptical-shaped soluble fiber lozenge 110A; (B) an elongated elliptical-shaped soluble fiber lozenge 110B; (C) semi-circular soluble fiber lozenge 110C; (D) square or rectangular-shaped soluble fiber lozenge 110D; (E) football-shaped soluble fiber lozenge 110E; (F) elongated rectangular-shaped soluble fiber lozenge 110F; (G) boomerang-shaped soluble fiber lozenge 110G; (H) rounded-edge rectangular-shaped soluble fiber lozenge 110H; (I) teardrop- or comma-shaped soluble fiber lozenge 110I; (J) bowtie-shaped soluble fiber lozenge 110J; (K) peanut-shaped soluble fiber lozenge 110K; and (L) flat-shaped soluble fiber lozenge. Alternatively, the soluble fiber lozenge can have different thicknesses or dimensionality, such that a beveled article (e.g., a wedge) is produced (see, for example, product 110M depicted in FIG. 1M) or a hemi-spherical shape is produced.

In addition or in the alternative to flavorants being included within the soluble-fiber matrix, flavorants can be included on an exterior of a soluble fiber lozenge provided herein. For example, referring to FIG. 1N, for example, some embodiments of a soluble fiber lozenge 110N can be equipped with flavor strips 116.

Figure 1O:
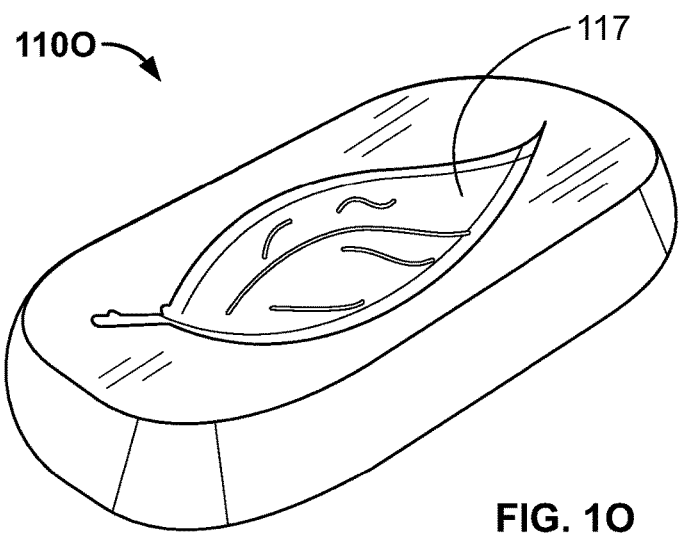

Referring to FIG. 1O, particular embodiments of a soluble fiber lozenge provided herein can be embossed or stamped with a design (e.g., a logo, an image, or the like). For example, soluble fiber lozenge 110O can be embossed or stamped with any type of design 117 including, but not limited to, a trademark, a product name, or any type of image. The design 117 can be formed directly into the soluble fiber lozenge, arranged along the exterior of the product 110O. The design 117 can also be embossed or stamped into those embodiments with a dissolvable film 116 applied thereto.

In some cases, the soluble fiber lozenges 110A-O can be wrapped or coated in an edible or dissolvable film, which may be opaque, substantially transparent, or translucent. The dissolvable film can readily dissipate when a soluble fiber lozenge provided herein is placed in an oral cavity. In some cases, a soluble fiber lozenge provided herein can be coated with a mouth-stable material. Exemplary coating materials include Carnuba wax, Beeswax, gelatin, acetylated monoglyceride, starch (e.g., native potato starch, high amylose starch, hydroxypropylated potato starch), Zein, Shellac, ethyl cellulose, methylcellulose, hydroxypropyl methylcellulose, carboxymethyl cellulose, and combinations thereof. Additives, such as miglycol, titanium dioxide, kaoline, bentonite, can be incorporated into the coating material to improve oxygen or moisture barrier and mechanical properties for the coating or film. For example, a coating can include a combination of gelatin and methylcellulose or gelatin and hydroxymethylcellulose. In some cases, the coating can contain sugar alcohols such as sorbitol, mannitol, xylitol, erythritol), disaccharide-derived (e.g., isomalt, lactitol, maltitol), or polysaccharide-derived mixtures (e.g., maltitol syrup, hydrogenated starch hydrolysates [HSH]) or combinations thereof. In some cases a coating material can contain sugar alcohols and hydroxymethylcellulose, gelatin, wax, with additives. In some cases, a coating material can include a plasticizer. In some case, a coating can include a colorant, a flavorant, and/or a one or more of the additives discussed above. In some cases, the body of a soluble fiber lozenge provided herein can have surfaces roughened to improve the adherence of a coating. In some cases, a coating can provide a glossy or semi-glossy appearance, a smooth surface, and/or an appealing visual aesthetic (e.g., a nice color). In some cases, the coating (e.g., a Beeswax, Zein, acetylated monoglyceride, and/or hydroxypropylated potato starch coating) can provide a soft mouth feel. In some cases, the coating (e.g., a methylcellulose, hydroxypropyl methylcellulose, carboxymethyl cellulose, ethyl cellulose, and/or gelatin coating) can provide a hard outer coating.

One or more soluble fiber lozenges 110 can be packaged in a variety of conventional and non-conventional manners. For example, a plurality of soluble fiber lozenges 110 can be packaged in a container having a lid. In some cases, a plurality of soluble fiber lozenges 110 can be stacked and packaged in a paper, plastic, and/or aluminum foil tube. In some cases, such as when soluble fiber lozenges provided herein include a therapeutic agent, the packaging can have a child-resistant lid.

Soluble Fiber Lozenge Properties

A soluble fiber lozenge provided herein can provide a favorable tactile experience (e.g., mouth feel). A soluble fiber lozenge provided herein can also retain its shape during processing, shipping, handling, and optionally during use. In some cases, a soluble fiber lozenge provided herein can be rigid. In some cases, a soluble fiber lozenge 110 can be brittle such that a consumer can crunch or masticate a soluble fiber lozenge provided herein in the consumer's mouth. A soluble fiber lozenge provided herein can be non-porous. Manipulation of a soluble fiber lozenge provided herein to increase the exposure of surfaces to saliva can accelerate a dissolution rate.

A soluble fiber lozenge provided herein can have a glass transition temperature (Tg) that is in the range of 50° C. to 120° C. (i.e., about 122° F. to about 248° F.), depending on formulas (e.g. soluble fiber type and weight percentage, water content, total flavor weight percentage, etc.) and processing conditions used to form a soluble fiber lozenge provided herein. The Tg can impact the preferred operating temperature used to form a solution of the soluble fiber, one or more additives, and other ingredients. By changing the soluble fiber weight percentage and type, the Tg range can be altered. In some cases, when a soluble fiber lozenge provided herein is placed in a consumer's mouth, the soluble fiber lozenge is not soft, but remains as an amorphous glassy state, as the consumer's body temperature is below the glass transition temperature range of the product. Soluble fiber lozenges provided herein can remain in a glassy state throughout the duration of its shelf life (e.g., at least 2 months, at least 6 months, at least 1 year, or at least 2 years). The Tg temperature can also impact a sensorial experience provided by a soluble fiber lozenge provided herein. For example, a glass transition temperature above body temperature can impede a soluble fiber lozenge from becoming sticky when placed in the consumers' mouth.

A soluble fiber lozenge provided herein can have any desirable color. In some cases, a soluble fiber lozenge provided herein can be translucent and have an off-white color. In some cases, a colorant can be included to provide a colorant a desired visual appearance. In some cases, natural and artificial colorants can be added to a soluble-fiber matrix of a soluble fiber lozenge 110. In some cases, a colorant can make a body of a soluble fiber lozenge opaque. For example, titanium dioxide can be added to a soluble-fiber matrix to produce an opaque white soluble fiber lozenge. Encapsulated flavors can be added during the extrusion process to create speckles, patterns or dots within the soluble fiber lozenge or on a surface of a soluble fiber lozenge 110. In some cases, a coating applied to a body of a soluble fiber lozenge can provide a desirable color.

Soluble Fibers

Soluble fiber dissolves in ambient water. Insoluble fiber does not dissolve in ambient water. Soluble fibers can attract water and form a gel. Not only are many soluble fibers safe for consumption, but some soluble fibers are used as a dietary supplement. As a dietary supplement, soluble fiber can slow down digestion and delay the emptying of a stomach. Instead of using soluble fiber as a mere additive, however, soluble fiber lozenges provided herein include a matrix of soluble fiber, which can dissolve to provide access to one or more additives included in the soluble-fiber matrix.

Any suitable soluble fiber or combination of soluble fibers can be used to form a soluble-fiber matrix provided herein. Suitable soluble fibers include maltodextrin, psyllium, pectin, guar gum, gum arabic, inulin, arabinoxylans, cellulose, and many other plant components such as resistant starch, resistant dextrins, lignin, pectins, beta-glucans, and oligosaccharides or a combination thereof. In some cases, a soluble fiber lozenge provided herein can include a digestion-resistant soluble fiber. A digestion resistant soluble fiber can include starch linkages that remain undigested by enzymes of the human digestive tract. In some cases, a soluble fiber lozenge provided herein can include a digestion-resistant maltodextrin. In some cases, a digestion-resistant maltodextrin can be derived from maze. Suitable maltodextrins can include those that are soluble in water up to 70% at 20° C., have a viscosity of about 15 cps for a 30% solution at 30° C., a DE in the range of about 6-16, and contain random $\alpha$-1,2, $\alpha$-1,3, $\alpha$-1,4, $\beta$-1,2, $\beta$-1,3 and $\beta$-1,4 glucose linkages in addition to the normal $\alpha$-1,4 glucose linkages found in partially hydrolyzed starch. See, e.g., U.S. Pat. Nos. 5,410,035; 5,380,717, which are hereby incorporated by reference. For example, Fibersol®-2 is a maltodextrin of DE 6-10 processed from corn starch using hydrochloric acid and enzymes, which can be used as the soluble fiber in a soluble fiber lozenge provided herein. Fibersol®-2 is partially indigestible because human digestive enzymes are incapable of digesting $\beta$ 1,2, $\beta$ 1,3 and $\beta$ 1,6 glucose bonds. See, e.g., U.S. Pat. No. 6,203,842. Other starch sources such as potato, rice, wheat, barley, peas, beans, lentils, oats, or tapioca can be processed to form digestion-resistant soluble fiber. A digestion resistant soluble fiber includes starch linkages that cannot be hydrolyzed by enzymes of the human digestive tract. In some cases, suitable soluble fibers include Pinefibre, Pinefibre C, Dexflow and Pineflow as discussed in U.S. Pat. No. 5,236,719, which is hereby incorporated by reference. Soluble fiber used in a soluble fiber lozenge provided herein can be GRAS by the Food and Drug Administration or another appropriate private, state, or national regulatory agency.

A soluble fiber lozenge body can include at least 40 weight percent of soluble fiber, at least 50 weight percent of soluble fiber, at least 60 weight percent of soluble, at least 70 weight percent of soluble fiber, at least 75 weight percent of soluble fiber, at least 80 weight percent of soluble fiber, at least 85 weight percent of soluble fiber, at least 90 weight percent of soluble fiber, or at least 95 weight percent of soluble fiber. In some cases, a soluble fiber lozenge body can include at least 40 weight percent maltodextrin, at least 50 weight percent maltodextrin, at least 60 weight percent maltodextrin, at least 70 weight percent maltodextrin, at least 75 weight percent maltodextrin, at least 80 weight percent maltodextrin, at least 85 weight percent maltodextrin, at least 90 weight percent maltodextrin, or at least 95 weight percent maltodextrin. In some cases, a soluble fiber lozenge body can include less than 90 weight percent maltodextrin, less than 85 weight percent maltodextrin, or less than 80 weight percent maltodextrin. In some cases, a soluble fiber lozenge body can include at least 40 weight percent digestion-resistant maltodextrin, at least 50 weight percent digestion-resistant maltodextrin, at least 60 weight percent digestion-resistant maltodextrin, at least 70 weight percent digestion-resistant maltodextrin, at least 75 weight percent digestion-resistant maltodextrin, at least 80 weight percent digestion-resistant maltodextrin, at least 85 weight percent digestion-resistant maltodextrin, at least 90 weight percent digestion-resistant maltodextrin, or at least 95 weight percent digestion-resistant maltodextrin.

Additives

A variety of additives can be included in a soluble fiber lozenge provided herein. The additives can include alkaloids (e.g., caffeine), minerals, vitamins, dietary supplements, nutraceuticals, energizing agents, soothing agents, coloring agents, amino acids, chemesthic agent, antioxidants, food grade emulsifiers, pH modifiers, botanicals (e.g., green tea), teeth whitening (e.g., SHMP), therapeutic agents, sweeteners, flavorants, and combinations thereof. A soothing agent provides a soothing sensation to the throat and oral cavity. Suitable soothing agents include, without limitation, chamomile, lavender, jasmine, and the like. Suitable chemesthic ingredients provide, without limitation, hot, spicy, or cooling flavors such as mint, menthol, cinnamon, pepper, and the like.

Energizing ingredients or vitamins include, without limitation, caffeine, taurine, guarana, vitamin B6, vitamin B12, and the like. According to certain embodiments, a soluble fiber lozenge provided herein includes caffeine. A caffeinated oral product can include synthetic caffeine and/or coffee-bean-extracted caffeine. In some cases, a caffeinated oral product includes coffee flavors and sweeteners. In some cases, the fibers in a caffeinated oral product are coffee bean fibers. According to some embodiments, an oral product can include between 10 and 200 mg of caffeine.

Soluble fiber lozenges provided herein can also include vitamins, dietary minerals, other dietary supplements, and/or therapeutic agents. For example, suitable vitamins include Vitamins A, B1, B2, B6, C, D2, D3, E, F, and K. For example, an oral product 110 can include C-vitamins with or without the presence of caffeine. Suitable dietary minerals include calcium (as carbonate, citrate, etc.) or magnesium (as oxide, etc.), chromium (usually as picolinate), and iron (as bis-glycinate). One or more dietary minerals could be included in an oral product with or without the use of other additives. Other dietary supplements and/or therapeutic agents can also be included as additives.

In some cases, a soluble fiber lozenge provided herein includes a therapeutic agent that is preferable absorbed transbuccally. For example, so therapeutic agents do not pass into the blood stream if they are swallowed. Exemplary therapeutic agents that can be included in an oral product 110 provided herein can include Gerd, Buprenorphin, Nitroglycerin, Diclofenac, Fentanyl, Carbamazepine, Galantamine, Acyclovir, Polyamidoamine Nanoparticles, Chlorpheniramine, Testosterone, Estradiol, Progesterone, Calcitonin, Fluorouracil, Naltrexone, Odansetron, Decitabine, Selegiline, Lamotrigine, and Prochlorperazine. For example, an oral product 110 can include Buprenorphine and be used for pain treatment. In some cases, an oral product 110 can include Nitroglycerin and be used for Angina Pectoris treatment. Because of the release properties of a soluble fiber lozenge provided herein, therapeutic agents included therein can be released at a rate such that a majority of the therapeutic agent is absorbed transbuccally, rather than swallowed.

A soluble fiber lozenge provided herein can also include fillers such as starch, di-calcium phosphate, lactose, sorbitol, mannitol, and microcrystalline cellulose, calcium carbonate, dicalcium phosphate, calcium sulfate, clays, silica, sodium lauryl sulfate (SLS), glyceryl palmitostearate, sodium benzoate, sodium stearyl fumarate, talc, and stearates (e.g., Mg or K), and waxes (e.g., glycerol monostearate, propylene glycol monostearate, and acetylated monoglycerides), stabilizers (e.g., ascorbic acid and monosterol citrate, BHT, or BHA), disintegrating agents (e.g., starch, sodium starch glycolate, cross caramellose, crosslinked PVP), pH stabilizers, or preservatives. In some cases, the amount of filler in a soluble fiber lozenge provided herein is limited to less than 10 weight percent in sum. In some cases, the amount of filler in a soluble fiber lozenge provided herein is limited to be less than 5 weight percent in sum. In some cases, the fillers are mouth stable. In some cases, the fillers can dissolve or disintegrate during use and thus result in an oral product that becomes more pliable during use.

In some cases, humectants can be added help maintain the moisture levels in a soluble fiber lozenge provided herein. Examples of humectants include glycerin and propylene glycol. In some cases, anti-microbial agents can be added to prevent spoilage and to lengthen shelf-life.

Sweeteners

A variety of synthetic and/or natural sweeteners can be used as additives in a soluble fiber lozenge provided herein. Suitable natural sweeteners include sugars, for example, monosaccharides, disaccharides, and/or polysaccharide sugars, and/or mixtures of two or more sugars. In some cases, a soluble fiber lozenge provided herein includes one or more of the following: sucrose or table sugar; honey or a mixture of low molecular weight sugars not including sucrose; glucose or grape sugar or corn sugar or dextrose; molasses; corn sweetener; corn syrup or glucose syrup; fructose or fruit sugar; lactose or milk sugar; maltose or malt sugar or maltobiose; sorghum syrup; mannitol or manna sugar; sorbitol or d-sorbite or d-sobitol; fruit juice concentrate; and/or mixtures or blends of one or more of these ingredients. A soluble fiber lozenge provided herein an also include non-nutritive sweeteners. Suitable non-nutritive sweeteners include: stevia, saccharin; aspartame; sucralose; or acesulfame potassium.

Flavorants

A soluble fiber lozenge provided herein can optionally include one or more flavorants as an additive. The flavorants can be natural or artificial. For example, suitable flavorants include wintergreen, cherry and berry type flavorants, various liqueurs and liquors (such as Dramboui, bourbon, scotch, and whiskey) spearmint, peppermint, lavender, cinnamon, cardamon, apium graveolents, clove, cascarilla, nutmeg, sandalwood, bergamot, geranium, honey essence, rose oil, vanilla, lemon oil, orange oil, Japanese mint, cassia, caraway, cognac, jasmin, chamomile, menthol, ylang ylang, sage, fennel, pimenta, ginger, chai, anise, coriander, coffee, liquorish, and mint oils from a species of the genus Mentha, and encapsulated flavors. Mint oils useful in particular embodiments of a soluble fiber lozenge provided herein include spearmint and peppermint. Synthetic flavorants can also be used. The particular combination of flavorants can be selected from flavorants that are GRAS in a particular country, such as the United States. Flavorants can also be included in the soluble fiber lozenge as encapsulated flavorants.

In some cases, the flavorants in a soluble fiber lozenge provided herein are limited to less than 20 weight percent in sum. In some cases, the flavorants in a soluble fiber lozenge provided herein are limited to be less than 10 weight percent in sum. For example, certain flavorants can be included in a soluble fiber lozenge provided herein in amounts of about 1 weight percent to 5 weight percent.

Cellulosic Fibers

Soluble fiber lozenges provided herein can optionally include cellulosic fibers within the soluble-fiber matrix. In some cases, soluble fiber lozenges 110 provided herein are substantially free of cellulosic fibers. As used here, "substantially free of cellulosic fibers" means that a soluble fiber lozenge provided herein has less than 0.5 weight percent cellulosic fibers. In some cases, soluble fiber lozenges 110 provided herein include up to 40 weight percent cellulosic fibers. Cellulosic fibers can be mixed with molten mixtures including soluble fibers to form a soluble fiber lozenge provided herein. Additives can be absorbed in cellulosic fibers. In some cases, the fibers are hydrophilic such that water-soluble additives can be wicked by the fibers. Cellulosic fibers can be derived from plant tissue. Suitable sources for cellulosic fibers include wood pulp, cotton, sugar beets, bran, citrus pulp fiber, switch grass and other grasses, Salix (willow), tea, and Populus (poplar). In some cases, the cellulosic fibers can be plant tissue comprising various natural flavors, sweeteners, or active ingredients. Cellulosic fibers can have a variety of dimensions. In some cases, cellulosic fibers in a soluble fiber lozenge provided herein can be processed to have an average fiber length of less than 200 micrometers. In some cases, cellulosic fibers in a soluble fiber lozenge provided herein have an average fiber length of between 25 and 125 micrometers. In some cases, cellulosic fibers are processed to have an average length of 75 micrometers or less.

Plasticizers

A soluble fiber lozenge provided herein can also include one or more plasticizers. Plasticizers can soften the final soluble fiber lozenge and thus increase its flexibility. Suitable plasticizers include propylene glycol, triacetin, glycerin, vegetable oil, partially hydrogenated oil, and medium chain triglycerides. Esters of polycarboxylic acids with linear or branched aliphatic alcohols of moderate chain length can also be used as plasticizers. Moreover, plasticizers can facilitate the extrusion processes described below. In some cases, a soluble fiber lozenge provided herein can include up to 20 weight percent plasticizer. In some cases, a soluble fiber lozenge provided herein includes between 0.5 and 10 weight percent plasticizer, a soluble fiber lozenge provided herein can include between 1 and 8 weight percent plasticizer, or between 2 and 4 weight percent plasticizer.

Production and Example

A soluble fiber lozenge provided herein can be produced by forming a molten mixture of soluble fiber, water, and under controlled heating conditions such that a solution of soluble fiber and water is formed without degrading the soluble fiber. In some cases, a temperature of the molten mixture is maintained at a temperature below 200° C. for a period of time (e.g., between 5 to 10 minutes or less). The molten mixture is then portioned into individual soluble fiber lozenges. Unlike many traditional lozenges, sugar and sugar alcohols are not required to obtain a firm smooth-dissolving texture in processes provided herein. Traditional lozenges can rely on the crosslinking of sugars or sugar alcohols due to caramelization caused by heating to caramelization temperatures. Caramelization temperatures, however, can degrade certain additives. A soluble-fiber matrix, however, can provide a soluble fiber lozenge provided herein with a suitable dissolution time when placed in a consumer's mouth.

Figure 2:
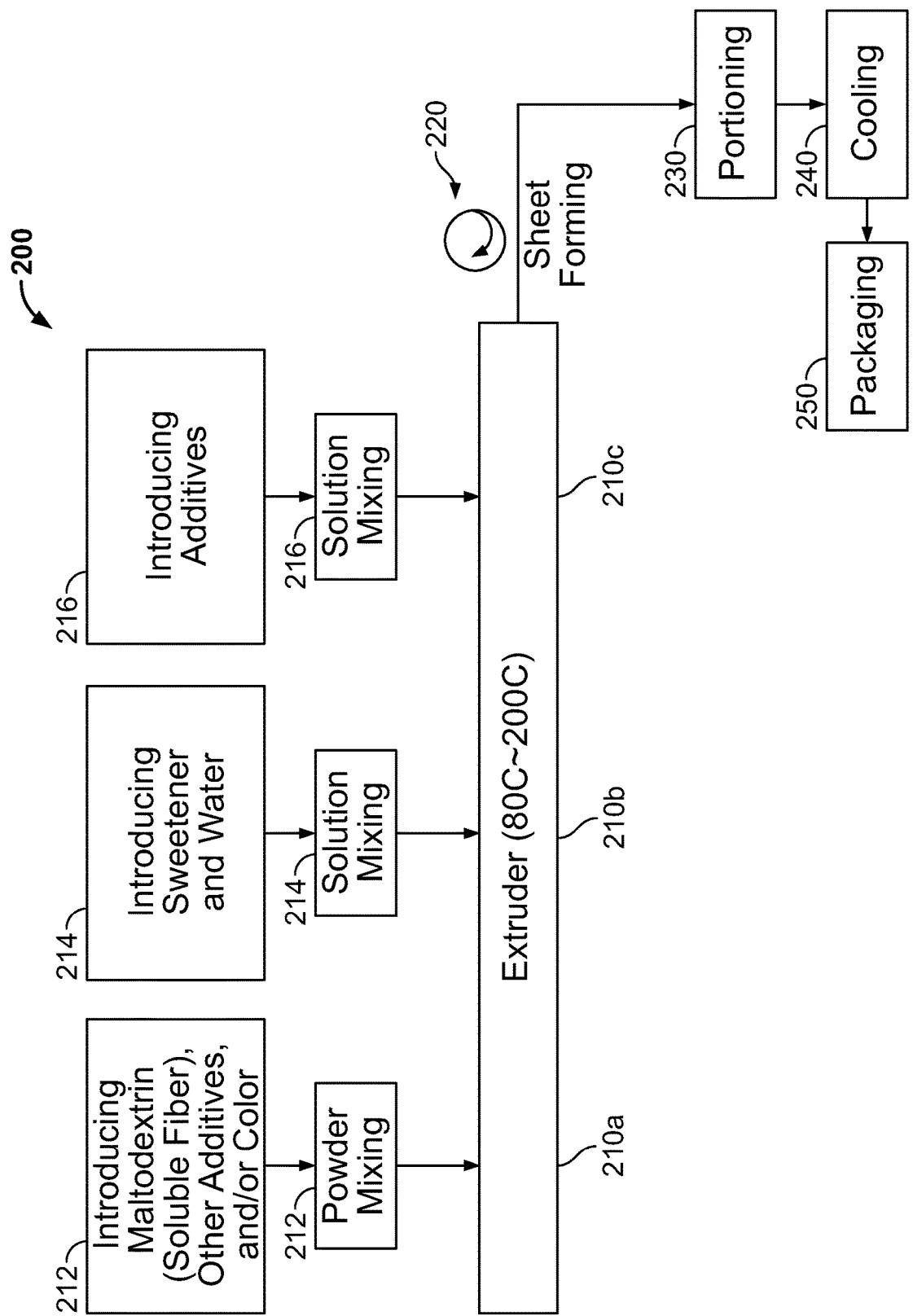
FIG. 2 depicts an exemplary process flow diagram for making soluble fiber lozenges provided herein.

A molten mixture can be mixed and heated in any suitable but controlled method. In some cases, such as shown in FIG. 2, ingredients for a molten mixture can be combined in an extruder and mixed in a continuous extrusion process. Unlike a traditional cooking method for many typical lozenges, a soluble fiber lozenge provided herein can have attributes precisely controlled by extruder operation parameters, such as feed rate, barrel temperature profile, screw design, rpms, etc.

Referring to FIG. 2, an exemplary method 200 for making soluble fiber lozenges provided herein can include adding dry ingredients 212 of soluble fiber (e.g., maltodextrin) and color (e.g., $TiO_2$) to a first station 210a of an extruder 210, adding a first group of solution ingredients 214, including water, at a second station 210b, and adding a second group of ingredients 216, including one or more additives, at a third station 210c. A mixing extruder 210 can include multiple stages controlled to be maintained at a predetermined temperature. Extruder 210 can include stages having temperatures ranging between 80° C. and 200° C. For example, dry ingredients 212 and first group of solution ingredients 214 can be mixed in a first stage of extruder 210, at a temperature of between 100° C. and 115° C., with one or more subsequent stages can have a higher temperature (e.g., between 115° C. and 200° C.). Second group of solution ingredients 216, including one or more additives, can be added downstream of the mixture of water with the soluble fiber. Adding certain ingredients downstream can limit degradation of certain ingredients due to exposure to heat. In some cases, the extrudate can have a total residence time of between 5 and 10 minutes in extruder 210.

Figure 3:
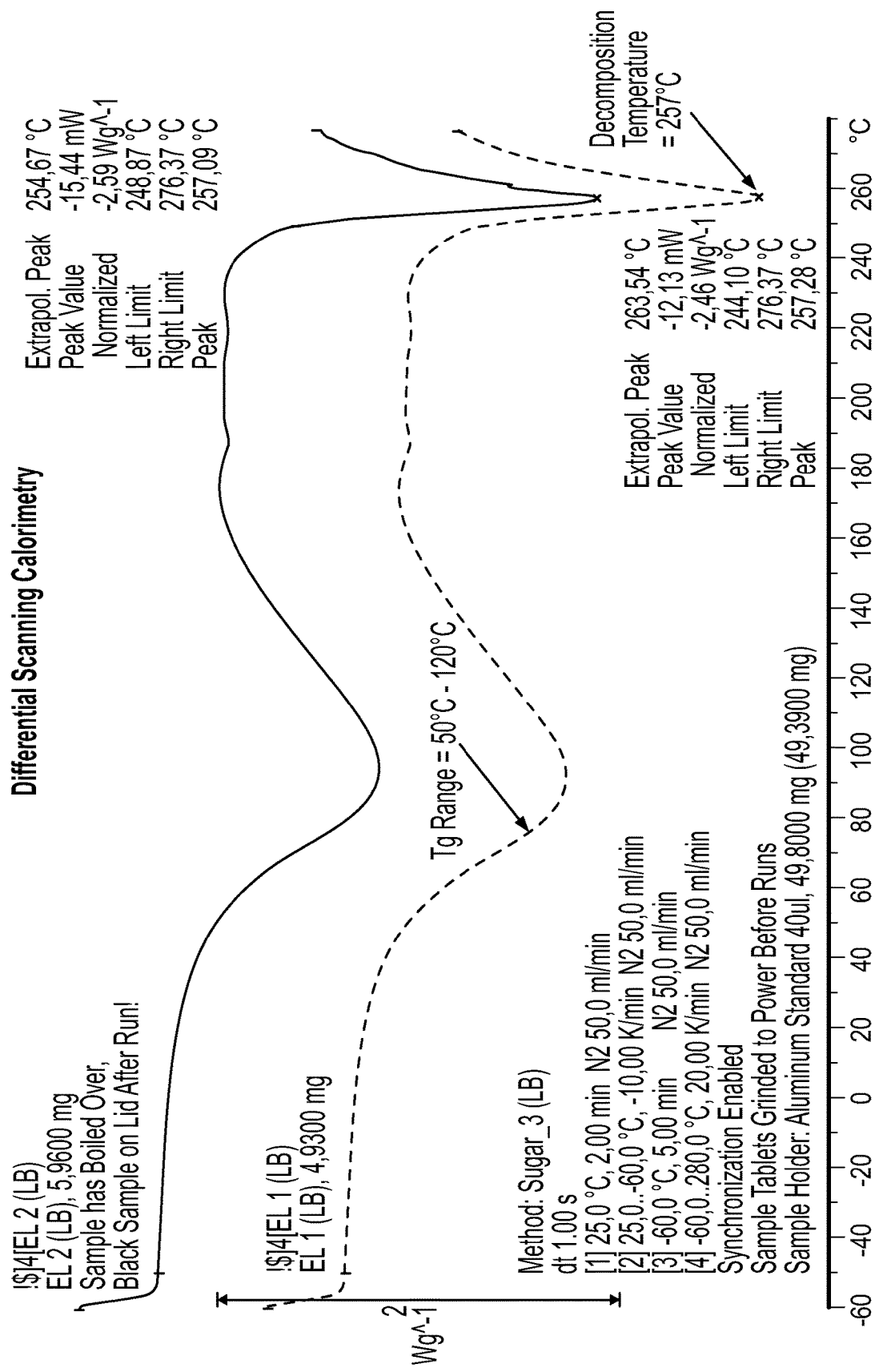
FIG. 3 is a differential scanning calorimetry data for an exemplary molten mixture provided herein.

A glass transition temperature (Tg) of molten mixture used to make a soluble fiber lozenge provided herein can range from 50° C. to 120° C. (i.e., about 122° F. to about 248° F.). FIG. 3 is a Differential Scanning calorimetry (DSC) Chart for an exemplary molten mixture provided herein, which shows a Tg for the mixture that has a Tg range of between 50° C. and 120° C.

A water content of a soluble fiber lozenge provided herein can be controlled in the extrusion process to ensure that the molten mixture has a glass transition temperature of greater than human body temperature. In some cases, a molten mixture can have a water content of less than 15 weight percent. In some cases, water content in a soluble fiber lozenge provided herein ranges from 2 weight percent to 15 weight percent. In some cases, water content in a soluble fiber lozenge provided herein ranges from 2 weight percent to 10 weight percent.

After passing through the extruder, a molten mixture provided herein can have a temperature of between its glass transition temperature and 200° C. In some cases, a molten mixture of between 85 and 90 weight percent digestion-resistant maltodextrin can reach a maximum temperature in an extruder of between 100° C. and 110° C. and exit the extruder at that temperature or lower. Because a molten mixture can remain above its glass transition temperature as it exits the extruder, the molten mixture can be reshaped after it exits the extruder. Molten mixture can pass onto a conveyor and move through a sheet forming apparatus 220. Sheet forming apparatus 220 can press the molten mixture into a sheet having a predetermined thickness. For example, a predetermined thickness can be between 2 mm and 10 mm.

Individual soluble fiber lozenges 110 can be cut from a sheet of molten mixture in portioning station 230. In some cases, a stamping die can cut one or more individual soluble fiber lozenges 110 to form a sheet. In some cases, a stamping die can press one or both sides of a sheet to both cut a soluble fiber lozenge and reshape edges to form rounded edges on the soluble fiber lozenges, such as those shown in FIG. 1. Cutting individual soluble fiber lozenges 110 can occur when the molten mixture is still above its Tg. Individual soluble fiber lozenges 110 can be cooled in a cooling station 240 and packaged in a packaging station 250.

In addition to extrusion, there are other methods for mixing and carefully controlling the temperature of a molten mixture used to form soluble fiber lozenges provided herein.

OTHER EMBODIMENTS

It is to be understood that, while the invention has been described herein in conjunction with a number of different aspects, the foregoing description of the various aspects is intended to illustrate and not limit the scope of the invention, which is defined by the scope of the appended claims. Other aspects, advantages, and modifications are within the scope of the following claims.

Disclosed are methods and compositions that can be used for, can be used in conjunction with, can be used in preparation for, or are products of the disclosed methods and compositions. These and other materials are disclosed herein, and it is understood that combinations, subsets, interactions, groups, etc. of these methods and compositions are disclosed. That is, while specific reference to each various individual and collective combinations and permutations of these compositions and methods may not be explicitly disclosed, each is specifically contemplated and described herein. For example, if a particular composition of matter or a particular method is disclosed and discussed and a number of compositions or methods are discussed, each and every combination and permutation of the compositions and the methods are specifically contemplated unless specifically indicated to the contrary. Likewise, any subset or combination of these is also specifically contemplated and disclosed.

What is claimed is:

1. A lozenge
  formed from a molten mixture heated to a maximum temperature of no more than 120° C., the lozenge comprising:
    soluble fibers in an amount of greater than or equal to 40 weight percent of the lozenge, the soluble fibers being non-cross-linked;
    triglycerides dispersed within the soluble fibers, the triglycerides present in an amount of less than 20 weight percent;
    water; and
    an additive, the lozenge having a glass transition temperature of greater than 37° C.

2. The lozenge of claim 1, wherein the glass transition temperature ranges from 50° ° C. to 100° C.

3. The lozenge of claim 1, wherein the glass transition temperature ranges from 80° C. to 100° C.

4. The lozenge of claim 1, wherein the lozenge is amorphous.

5. The lozenge of claim 1, wherein the triglycerides include medium chain triglycerides.

6. The lozenge of claim 1, wherein the triglycerides are present in an amount ranging from 0.5 weight percent to 10 weight percent.

7. The lozenge of claim 1, wherein the water is present in an amount ranging from less than 15 weight percent.

8. The lozenge of claim 1, wherein the water is present in the lozenge in an amount ranging from 3 weight percent to 10 weight percent.

9. The lozenge of claim 1, wherein the soluble fibers are present in an amount ranging greater than or equal to 60 weight percent.

10. The lozenge of claim 1, wherein the soluble fibers are present in an amount ranging greater than or equal to 80 weight percent.

11. The lozenge of claim 1, wherein the soluble fibers include digestion-resistant soluble fibers.

12. The lozenge of claim 1, wherein the soluble fibers include maltodextrin, psyllium, inulin, an arabinoxylan, cellulose, resistant starch, a resistant dextrin, lignin, a pectin, a beta-glucan, an oligosaccharide, or any combination thereof.

13. The lozenge of claim 1, wherein the lozenge is free of sugars and sugar alcohols.

14. The lozenge of claim 1, wherein the lozenge is free of cellulosic fibers.

15. The lozenge of claim 1, wherein the additive includes a mineral, a vitamin, a dietary a supplement, a nutraceutical, an energizing agent, a soothing agent, an amino acid, a chemesthetic agent, an antioxidant, a botanical, a teeth whitening agent, a therapeutic agent, or any combination thereof.

16. The lozenge of claim 1, wherein the additive includes an alkaloid.

17. The lozenge of claim 1, wherein the additive includes a flavorant.

18. The lozenge of claim 1, wherein the additive includes a sweetener.

19. The lozenge of claim 1, further comprising:
  a body including,
    the soluble fibers,
    the triglycerides, and
    the additive; and
  a coating on a surface of the body.

* * * * *